United States Patent [19]

Van Der Marel et al.

[11] Patent Number: 5,192,539

[45] Date of Patent: Mar. 9, 1993

[54] INFECTIOUS BURSAL DISEASE VIRUS PRODUCTION IN CONTINUOUS CELL LINES

[75] Inventors: Piet Van Der Marel, Venray; Pieter G. Mooren, Kronenberg, both of Netherlands

[73] Assignee: Akzo N.V., Arnhem, Netherlands

[21] Appl. No.: 350,656

[22] Filed: May 11, 1989

[30] Foreign Application Priority Data

Jul. 21, 1988 [NL] Netherlands .................. 88 01843

[51] Int. Cl.$^5$ .......................... A61K 39/12; C12N 7/00
[52] U.S. Cl. ........................................ 424/89; 424/88; 435/235.1; 435/236; 435/237; 435/239; 435/240.1; 435/240.27; 530/826
[58] Field of Search ............... 424/89, 88; 435/235.1, 435/236, 237, 239, 240.1, 240.27; 530/826

[56] References Cited

U.S. PATENT DOCUMENTS

| | | | |
|---|---|---|---|
| 4,110,433 | 8/1978 | Purdy, III | 424/89 |
| 4,530,831 | 7/1985 | Lütticken et al. | 424/89 |
| 4,824,668 | 4/1989 | Melchior, Jr. et al. | 424/89 |
| 4,956,452 | 9/1990 | Snyder et al. | 424/89 |

OTHER PUBLICATIONS

Kibenge et al., *Avian Diseases*, vol. 32, pp. 298–303 (1988).
Jackwood, et al., *Avian Diseases*, vol. 31, No. 2, pp. 371–375 (1987).
Lukert et al., *American Journal of Veterinary Research*, vol. 36, No. 4 pp. 539–540 (1975).
Fields et al., (Ed)., Fundamental Virology, Second Edition, p. 26, N.Y. Raven Press (1991).

*Primary Examiner*—Johnnie R. Brown
*Assistant Examiner*—Abdel A. Mohamed
*Attorney, Agent, or Firm*—William M. Blackstone

[57] ABSTRACT

Infectious bursal disease virus vaccine free of avian cell material comprising inactivated virus or live virus that induces a protective immune response when administered to poultry by noninjection means.

11 Claims, No Drawings

INFECTIOUS BURSAL DISEASE VIRUS PRODUCTION IN CONTINUOUS CELL LINES

The invention relates to the use of permanent mammalian cell lines for the multiplication of the infectious bursal disease virus (IBDV), which is infectious to birds, and of IBDV antigen.

Avian viruses are usually produced in embryonated eggs, on bird cell substrates derived from embryonated eggs, such as primary or secondary chicken embryo fibroblasts (CEF), primary chicken liver cells or chicken kidney cells, or in organs of live animals, such as in the bursa of Fabricius. Viruses from sources of this type are used throughout the world for the preparation of inactivated and live vaccines.

The principal disadvantage in using animals and embryonated eggs for the preparation of vaccines is the uncertainty with regard to the quality of these. Even specific pathogen-free chickens can unexpectedly become infected, making them unsuitable for vaccine prodution. Occasionally an infection of this type remains undetected for some time.

The use of a permanent cell line could provide an ideal solution to this problem. However, chicken cell lines, which are suitable for vaccine production, have not been available up to now. The majority of bird cell lines consist of lymphoblastoid cells, which are obtained from animals with lymphoid leucosis or Marek's disease.

Attempts to develop permanent cell lines from normal chicken embryo fibroblasts have not proved successful. Cell lines have occasionally been developed from normal embryos, but in all cases these were afterwards found to contain retrovirus genomes, and some even to shed virus particles.

It has now been found that IBDV strains which can grow on cell cultures of chicken embryo fibroblast (such as the D78 and SP strains) can also be cultured efficiently in mammalian cell lines. It has been found that it is not necessary to adapt the viruses to the mammalian substrate. Moreover, it has been found that the yields in mammalian cells are frequently much higher than in the CEF system. Virus yields are usually expressed in "infectious virus particles per unit volume" ($EID_{50}$/ml; $TCID_{50}$/ml). Another way to quantify virus yields is to determine the antigen mass. Using immunochemical techniques such as ELISA the antigen content of a virus preparation can be compared with that of a standard preparation, to which a fixed value of antigen mass units has been assigned. With both types of method of determination, mammalian cell line systems give much higher yields than the CEF system.

Furthermore, it is surprising that these favourable yields are achieved at cell concentrations which are lower than those conventionally employed for antigen production on CEF. The optimum cell concentration in the mammalian cell system is 3-6 times lower than that which is customarily used for production on CEF. These results show that mammalian cells in general are better substrates for IBDV than CEF. At the same time it was found that the virus antigen prepared in this way is at least as effective in a vaccine as antigen produced on CEF.

Suitable mammalian cell lines for IBDV production according to the invention are, for example, Vero cells, chimpanzee liver cells, buffalo vervet cells and mouse 3T3 cells.

Stationary culture systems in cell culture flasks and roller flasks can be used for the culture of mammalian cells. Other, usually larger scale, cell culture systems are stirred vessels (fermenters) for the culture of anchorage-independent cells, microcarrier systems for the culture of anchorage-dependent cells and hollow fibre systems for the culture of both types of cell. In addition, there is a multiplicity of other stationary systems for the culture of anchorage-dependent cells. A common feature of the latter systems is that they have a very large surface for cell attachment.

The culture of mammalian cells requires the use of complex culture fluids. These commonly consist of a base fluid (medium), which is chemically well defined, and one or more additives, which are chemically less well defined. The additives are usually protein-rich solutions, such as serum and protein hydrolysis products. Serum is virtually indispensable for cell growth and cell division. Foetal calf serum (FoCS) or fasting calf serum (FaCS) is added to most culture systems in a concentration of 1-10% (V/V). Only in special cases it is possible, after a period of adaptation, to culture mammalian cells in serum-free or even protein-free culture medium.

The IBD viruses according to the invention can be incorporated in vaccines as live viruses, if desired after prior attenuation, or as inactivated viruses.

The vaccines containing live virus can be prepared and marketed in the form of a suspension, or lyophilized.

Lyophilized vaccines can preferably contain one or more stabilizers. Suitable stabilizers are, for example, SPGA (Bovarnik (1950): J. Bacteriology 59; 509), carbohydrates (such as sorbitol, mannitol, starch, sucrose, dextran or glucose), proteins (such as albumin or casein), or degradation products thereof, protein-containing materials (such as bovine serum or skimmed milk) and buffers (such as alkali metal phosphates). If desired, one or more compounds with an adjuvant action can also be added. Suitable compounds for this purpose are, for example, aluminium hydroxide, phosphate or oxide, mineral oil (such as Bayol F ®, Marcol 52 ®) and saponins.

The aim of inactivation of IBD viruses is to eliminate both reproduction and virulence of the viruses. In general, this can be achieved by chemical or physical means. Chemical inactivation can be effected by treating the viruses with, for example, enzymes, formaldehyde, $\beta$-propiolactone, ethylene-imine or a derivative thereof, an organic solvent (such as a halogenated hydrocarbon) and/or a detergent (such as Tween ®, Triton X ®, sodium desoxy-cholate, sulphobetain or cetyl trimethylammonium salts). If necessary, inactivating substance is neutralized afterwards; material inactivated with formaldehyde can, for example, be neutralized with thiosulphate. Physical inactivation can preferably be carried out by subjecting the viruses to energy-rich radiation, such as UV light, X-radiation or $\gamma$-radiation. If desired, the pH can be brought back to a value of about 7 after treatment.

Usually, an adjuvant (for example such as mentioned above), and, if desired, one or more emulsifiers, such as Tween ® and Span ®, is also added to the inactivated virus material.

The vaccines according to the invention are suitable for protecting poultry (such as chickens and turkeys) against IBD (Gumboro's disease).

The vaccines according to the invention can, for example, be administered by means of intramuscular, subcutaneous or in ovo injection, eyedrops, nosedrops, or drinking water or in the form of sprays.

The invention also includes combination vaccines with the IBDV material according to the invention. For inactivated vaccines, this IBDV material can be combined with antigen material of Newcastle Disease Virus, Infectious Bronchitis Virus, Egg Drop Syndrome Virus, Reovirus, bacteria (such as Escherichia coli) and/or parasites (such as Eimeria species). The combinations with New castle Disease Virus and/or Marek Virus are very suitable for live combination vaccines.

Examples Preparation of IBDV on mammalian cell lines Cell culture

Cell stocks were stored in glass ampoules in liquid nitrogen. To start a cell culture the contents of an ampoule were rapidly thawed and slowly diluted with cell culture medium. The cell suspension was centrifuged at low speed to remove the DMSO in the refrigerant. The sedimented cells were resuspended in complete cell culture medium and the cells were seeded in suitable culture vats. Usually, the cells were cultured in a mixture of M 199/F10 medium in a ratio of 1:1, or in MEM, supplemented with tryptose phosphate broth. The medium contained 2–10% FoCS and, if desired, antibiotics and a fungicide. The cells were cultured at 37° C. in stationary culture (tissue culture flasks) or in roller flasks (490 $cm^2$). After the cells had reached a density such that they formed a dense monolayer, the cells were treated with trypsin for the preparation of subcultures.

Virus production, harvest and inactivation

Freeze-dried seed virus was redissolved or deep-frozen seed virus was thawed and diluted with cell culture medium to a concentration at which it is possible to divide the seed virus in the correct portions. The cells were infected in a M.O.I. (multiplicity of infection) ratio of $10^0$–$10^{-4}$ $TCID_{50}$/cell.

If desired, seed virus was added directly after seeding the cells.

The infected cells were incubated for up to 10 days. Usually, the virus was harvested 2–10 days after virus infection. The supernatant liquor in the culture vats was collected and inactivated with formalin. For this purpose, formaldehyde was added to the cell suspension until a concentration of 0.05–0.2% was reached. The mixture was incubated for 1–3 days at 20°–22° C.

Vaccine production

For use as a vaccine, inactivated IBDV antigen was introduced into a water-in-oil emulsion (Marcol 52 ®).

Production of IBDV on primary chicken embryo fibroblasts (CEF) Preparation of CEFs CEFs were prepared from 10–11-day-old, specific pathogen-free, incubated eggs in accordance with the method known to those skilled in the art.

Culture of CEFs

CEFs were cultured in the same media as were used for culture of the continuous cell lines. FoCS or FaCS was added to the media until the concentration reached 5%. A concentrated cell suspension, obtained after trypsin treatment, was diluted with cell culture medium to a concentration of 0.5–$10\times10^6$ cells/ml. The cell suspension was transferred to tissue culture flasks or roller flasks. The cells were incubated for approximately 24 hours at a temperature of 37°–39.5° C., after which a dense monolayer had formed.

Production, harvesting and inactivation of virus

Freeze-dried seed virus was dissolved and diluted with cell culture medium to a volume sufficiently large to divide into suitable amounts for seeding on cells. The virus was added in a concentration of $10^0$–$10^{-5}$ $TCID_{50}$/cell. If desired, seed virus was added directly after seeding the cells.

The infected cells were incubated for 48–96 hours. The supernatant liquor was then collected from the culture vats and inactivated with 0.2% formaldehyde for 24 hours at room temperature.

Determination of IBDV antigen mass

IBDV antigen was determined with the aid of a quantitative sandwich ELISA;

1. microtitre plates were coated with IBDV-specific antibody;
2. the wells were filled with dilution series of the antigen samples and incubated;
3. the wells were then incubated with IBDV-specific antibody which is conjugated with enzyme;
4. subsequently a substrate for the enzyme was added to the wells;
5. after some time the enzyme reaction in the wells was stopped with dilute sulphuric acid and the colour intensity of the contents of the wells determined spectrophotometrically.

The absorptions measured were compared with those of a dilution series of a standard antigen preparation of a known concentration. The antigen mass values were expressed in ELISA units/ml (EU/ml).

Virus titration

Determination of the infectious virus titre was carried out on primary chicken embryo fibroblasts in microtitre plates. A ten-fold dilution series of the samples was first made in a primary CEF suspension which contains $5\times10^5$ cells/ml. The wells of the microtitre plates were then filled with, in each case, 200 μl of the dilution series of the sample; each sample was tested 6–10 times. The plates were incubated for 4–7 days at 37°–39° C. in a $CO_2$ incubator, after which they were examined microscopically for the occurrence of cytopathic effects. The titre was calculated in $TCID_{50}$/ml Usually, the virus titres were expressed as $^{10}$log $TCID_{50}$/ml.

Determination of virus-neutralizing antibodies

Virus-neutralizing antibodies were determined in a microneutralization test in microtitre plates. For this purpose duplicate dilution series of the serum samples were incubated with 1,000 $TCID_{50}$ of the IBDV in a serumfree cell culture medium for 1–2 hours at 37° C. in a $CO_2$ incubator. $10^5$ primary chicken embryo cells in complete cell culture medium were then introduced into each well. The plates were incubated for 4–7 days at 37° C. in a $CO_2$ incubator, after which they were examined under a microscope for the occurrence of cytopathic effects. The virus neutralization (VN) titre was now defined as the reciprocal of the highest dilution at which the cytopathic effect is completely absent. Usually, the VN titres were expressed as $^2$log VN titre.

EXAMPLE 1 Production of D78 antigen on a large scale on primary chicken embryo fibroblasts CEFs were obtained from 11-day-old specific pathogen-free chicken embryos. These cells were seeded in 1,585 cm$^2$ glass roller flasks in a concentration of 1-3×10$^6$ cells/ml in M199/F10 cell culture medium supplemented with 5% FaCS. 300 ml cell suspension were used per flask.

The flasks were incubated for 18-24 hours at 38.5°-39.5° C. Seed virus and an extra quantity of cells were then added to the flasks. 100 ml suspension containing 3-9×10$^6$ cells/ml and 10$^{4-106}$ TCID50 of D78 seed virus were used per roller flask. The roller flasks were then incubated for a further 48-120 hours at 38.5°-39.5° C., after which the virus suspension was harvested and inactivated with formaldehyde. The results of the antigen mass determinations on eight representative production batches are summarized in Table 1.

TABLE 1

| Antigen mass (EU/ml) | | |
|---|---|---|
| lowest value | highest value | mean |
| 397 | 1996 | 946 |

EXAMPLE 2 Preparation of D78 antigen on primary chicken embryo fibroblasts under optimized laboratory conditions CEFs were obtained from 11-day-old specific pathogen-free chicken embryos. The cells were seeded in 490 cm$^2$ plastic roller flasks in concentrations of 1.5, 3.0 and 6.0×10$^6$ cell/ml in M199/F10 cell culture medium supplemented with 5% FoCS. 100 ml cell suspension were used per flask.

At the same time 10$^{7.3}$ TCID50 seed virus was added to each flask, resulting in infection amounts of 0.12, 0.06 and 0.03 TCID$_{50}$/cell respectively. The roller flasks were incubated at 37° C. Samples were taken after incubating for two days and harvesting was on the third day. The antigen mass was determined using ELISA in both the samples and the harvested material. The results are given in Table 2.

TABLE 2

| Initial cell concentration | Antigen mass (EU/ml) | | Antigen mass/10$^6$ cells (EU/10$^6$ cells) | |
|---|---|---|---|---|
| | 2 days p.i. | 3 days p.i. | 2 days p.i. | 3 days p.i. |
| 1.5 × 10$^6$ | 2779 | 3218 | 1852 | 2145 |
| 3.0 × 10$^6$ | 4353 | 5361 | 1451 | 1787 |
| 6.0 × 10$^6$ | 6467 | 6652 | 1078 | 1109 |

Conclusion: under optimized laboratory conditions it is possible substantially to improve the production of antigen mass on CEF, but the production per cell is considerably reduced when the cell concentration is increased.

EXAMPLE 3 Preparation of IBDV antigens on Vero cells A. Infection on a fully grown monolayer Vero cells were seeded in two 490 $cm^2$ roller flasks in a concentration of $0.25\times10^6$ cells/ml. 100 ml cell suspension in Eagle's MEM supplemented with tryptose phosphate broth and 5% FoCS were added to each roller flask. One flask was incubated for 4 days and the other for 5 days at 37° C. The cell culture medium was then removed and D78 seed virus was added in a quantity of $10^6$ $TCID_{50}$ per roller flask. After incubation of the cell-virus mixture for 30 minutes at 37° C., 100 ml of cell culture medium were added. After a further incubation for eight or seven days respectively, the virus suspension was harvested and the antigen mass determined. This was found to be 19413 EU/ml after seven days' incubation and 19706 EU/ml after eight days.

B. Infection of cells with IBDV in suspension

Vero cells were seeded in 490 $cm^2$ plastic roller bottles in a concentration of $1\times10^6$ cells/ml in Eagle's MEM supplemented with tryptose phosphate broth and 5% FoCS. 100 ml of cell suspension were used per flask. The IBD seed virus, strain D78 or SP, was also added immediately after the cells.

The cultures were incubated for 7 days. Samples were taken 45, 96 and 144 hours after infection. The antigen mass contents of these samples were determined with the aid of ELISA (Table 3).

TABLE 3

| Virus strain | M.O.I. $TCID_{50}$/cell | Antigen mass (EU/ml) after: 45 h | 96 h | 144 h | Antigen mass/$10^6$ seeded cells ($EU/10^6$ cells) after 144 h |
|---|---|---|---|---|---|
| D78 | $10^{-1}$ | 9044 | 20737 | 22937 | 22937 |
| D78 | $10^{-2}$ | 1197 | 20016 | 17759 | 17739 |
| D78 | $10^{-3}$ | 161 | 13224 | 18233 | 18233 |
| SP | $10^{-1}$ | 3543 | 28439 | 26883 | 26883 |
| SP | $10^{-2}$ | 509 | 21799 | 23165 | 23165 |
| SP | $10^{-3}$ | 64 | 15121 | 13934 | 13934 |

Conclusion: production of IBDV on mammalian cells yields antigen masses in approximately ten times the yield obtained by production on CEF under comparable conditions in accordance with Example 2. Approximately equal production levels were achieved on monolayers and in suspension culture.

EXAMPLE 4 Infectious virus titre of IBDV produced on Vero cells

Vero cells were seeded in 490 $cm^2$ roller flasks in a concentration of $1\times10^6$ cells/ml 100 ml cell suspension in Eagle's MEM supplemented with tryptose phosphate broth and 5% FoCS were introduced into each roller flask. At the same time, D78 or SP seed virus was added in an amount of 0.01 $TCID_{50}$/cell. The flasks were incubated at 37° C. During incubation samples were taken and the antigen mass and infectious virus contained therein determined. The antigen mass was determined (EU/ml) using ELISA. The infectious virus titre was determined in a microtitre plate test with the aid of primary CEFs ($^{10}\log$ $TCID_{50}$/ml) The results are given in Table 4:

TABLE 4

| Virus strain | Yield | | | | | |
|---|---|---|---|---|---|---|
| | 45 hours p.i. | | 96 hours p.i. | | 144 hours p.i. | |
| | EU/ml | $^{10}$log TCID$_{50}$/ml | EU/ml | $^{10}$log TCID$_{50}$/ml | EU/ml | $^{10}$log TCID$_{50}$/ml |
| SP | 1197 | 8.9 | 20016 | 10.2 | 17739 | 9.9 |
| D78 | 509 | 8.2 | 21799 | 9.7 | 23165 | 9.5 |

EXAMPLE 5 Live vaccine

Two groups of four SPF chickens (age three weeks) were vaccinated on day 0 with live IBD virus, strain D78, produced on Vero cells. The virus was administered ocularly to the birds in a volume of 0.1 ml. One group received $10^6$ TCID$_{50}$ per bird and the other $10^{4.5}$ TCID$_{50}$ per bird. In addition, a group of four birds was vaccinated in the same way with a D78 vaccine produced on primary CEFs. Blood was taken sixteen days after vaccination. This was examined for the presence of IBDV-neutralizing antibodies.

The result is given in Table 5.

TABLE 5

| Vaccine | Dose ($^{10}$log TCID$_{50}$/bird) | Serum neutralization titre ($^2$log VN) |
|---|---|---|
| D 78/Vero | 6.0 | 9.1 ± 1.5[1] |
| D 78/Vero | 4.5 | 10.6 ± 1.4 |
| D 78/CEF | 5.7 | 10.2 ± 1.8 |

[1] $^2$log VN ± standard deviation

The same experiment also involved a number of birds from which the bursa was removed 3, 6 and 16 days after vaccination and examined histologically for acute and subacute lesions. No discrepancies were found between bursas from birds vaccinated with virus produced on CEF and those of birds vaccinated with virus produced on Vero cells.

Conclusion: live IBD vaccine produced on Vero cells is just as immunogenic and just as harmless as live IBD vaccine produced on CEF.

EXAMPLE 6 Preparation of IBDV strain D78 in a chimpanzee liver cell line 100 ml of a suspension of chimpanzee liver cells (concentration $0.6\times10^6$ cells/ml) were seeded in a 490 $cm^2$ roller flask. IBDV seed virus (strain D78) was added in a concentration of $10^{-4}$ $TCID_{50}$/cell. After incubating for seven days, the antigen mass content was 27042 EU/ml, corresponding to approximately $45\times10^3$ EU/$10^6$ seeded cells.

EXAMPLE 7 Preparation of IBDV strain D78 in a mouse cell line 100 ml of a suspension of NIH3T3 mouse cell (concentration $0.3\times10^6$ cell/ml) were seeded in a 490 $cm^2$ roller flask, after which IBD seed virus (strain D78) was added in a concentration of $10^{-4}$ $TCID_{50}$/ cell. After incubating for seven days, the antigen mass content of the virus was 3514 EU, which corresponds to approximately $12\times10^3$ EU/$10^6$ seeded cells.

EXAMPLE 8 Comparison of the immunogenicity of IBDV antigens cultured in CEF or Vero cells D78 and SP antigens prepared in primary CEFs or in Vero cells were inactivated with formalin and emulsified in mineral oil. Four-week-old specific pathogen free chickens (white Leghorns) were each vaccinated intramuscularly with 0.5 ml of one of the abovementioned emulsions. Six weeks after vaccination blood was taken from these chickens, the sera were inactivated for 30 minutes at 56° C. and the virus-neutralizing antibodies contained therein were determined on primary CEFs. The results are summarized in Table 6.

TABLE 6

| Virus antigen | Production cell | Antigen mass | Neutralizing antibody titre(1) ($^2$log VN) |
|---|---|---|---|
| D78 | CEF | 2924 | 14.4 ± 1.3 |
| D78 | CEF | 1072 | 13.7 ± 1.7 |
| D78 | Vero | 2750 | 14.6 ± 1.5 |
| D78 | Vero | 690 | 13.1 ± 1.9 |
| SP | Vero | 4000 | 14.6 ± 1.1 |
| SP | Vero | 1000 | 13.5 ± 1.3 |

(1)mean for 10 birds ± standard deviation

EXAMPLE 9 Comparison of the effectiveness of vaccination with IBDV antigens cultured in CEF or Vero cells Eight-week-old chickens were vaccinated in groups of 10 with inactivated D78-oil emulsion vaccine. 0.5 ml vaccine was administered intramuscularly to each bird. One group of birds was vaccinated with antigen produced on Vero cells and two groups with antigen produced on CEF. Both antigens were produced in roller flasks in accordance with the procedure described in Examples 2 and 3. Six weeks after vaccination, serum was collected from the birds and examined for virus-neutralizing antibodies. The results are summarized in Table 7.

TABLE 7

| Vaccine | $^2$log VN ± stand. dev. |
|---|---|
| D78/CEF1 | 11.2 ± 1.4 |
| D78/CEF2 | 13.1 ± 0.9 |
| D78/Vero | 14.5 ± 1.7 |

Statistic analysis showed that the titre induced by D78/Vero was significantly higher than that induced by D78/CEF (Student's T test; $p<0.05$ of CEF2).

We claim:

1. A line infectious bursal disease virus (IBDV) vaccine free of avian cell material comprising IBDV derived from a mammalian cell line infected with IBDV, wherein said vaccine induces a protective immune response when administered to poultry in a medium selected from the group consisting of eye drops, nose drops, drinking water and sprays.

2. An IBDV vaccine according to claim 1, wherein the mammalian cell line is an ape cell line.

3. An IBDV vaccine according to claim 2, wherein the ape cell line is a Vero cell line.

4. A method for the immunization of poultry against infectious bursitis, comprising administering a vaccine according to claim 1 to poultry in a medium selected from the group consisting of eye drops, nose drops, drinking water and sprays.

5. A method according to claim 4, comprising administering the vaccine in drinking water.

6. An IBDV vaccine according to claim 1, wherein the vaccine induces a protective immune response when administered to poultry in drinking water.

7. A method for the preparation of live IBDV vaccine comprising:
(a) culturing IBDV in a mammalian cell line,
(b) harvesting live virus from the cultured cell line, and
(c) subjecting the harvested live virus to at least one of the following treatments:
  i. adding a pharmaceutically acceptable carrier or diluent,
  ii. adding adjuvant,
  iii. lyophilizing,
the live vaccine is effective in inducing a protective immune response when administering to poultry in a medium selected from the group consisting of eye drops, nose drops, drinking water and sprays.

8. The method according to claim 7, wherein the vaccine induces a protective immune response when administered in drinking water.

9. The method according to claim 7, wherein the virus is cultured on an ape cell line.

10. The method according to claim 9, wherein the virus is cultured on a Vero cell line.

11. The method according to claim 7, wherein at least one other immunogen of another avian pathogen not related to IBDV is incorporated into the vaccine, the immunogen is selected from the group consisting of Newcastle Disease Virus, Infectious Bronchitis Virus, Marek's Disease Virus, Egg Drop Syndrome Virus, Reo Virus, *E. coli* and Eimeria.

* * * * *

UNITED STATES PATENT AND TRADEMARK OFFICE
CERTIFICATE OF CORRECTION

PATENT NO. : 5,192,539

DATED : March 9, 1993

INVENTOR(S) : Piet van der Marel et al.

It is certified that error appears in the above-identified patent and that said Letters Patent is hereby corrected as shown below:

Column 8

Claim 1, line 1, after "A", delete "line and replace with -- live --.

Signed and Sealed this

Twenty-third Day of November, 1993

Attest:

BRUCE LEHMAN

Attesting Officer     Commissioner of Patents and Trademarks